US00PP29001P2

(12) United States Plant Patent
Arts

(10) Patent No.: US PP29,001 P2
(45) Date of Patent: Feb. 27, 2018

(54) ***MANDEVILLA* PLANT NAMED 'MAN216901'**

(50) Latin Name: *Mandevilla sanderi*
Varietal Denomination: MAN216901

(71) Applicant: Niels Arts, Aalsmeer (NL)

(72) Inventor: Niels Arts, Aalsmeer (NL)

(73) Assignee: MBA B.V., De Kwakel (NL)

( * ) Notice: Subject to any disclaimer, the term of this patent is extended or adjusted under 35 U.S.C. 154(b) by 0 days.

(21) Appl. No.: 15/330,233

(22) Filed: Aug. 27, 2016

(51) Int. Cl.
*A01H 5/02* (2006.01)

(52) U.S. Cl.
USPC ..... Plt./232

(58) Field of Classification Search
USPC ..... Plt./232
See application file for complete search history.

(56) References Cited

PUBLICATIONS

UPOV hit on *Mandevilla* plant named 'Man216901', QZ PBR 20160930, application filed Apr. 14, 2016.*

* cited by examiner

*Primary Examiner* — Anne M Grunberg
(74) *Attorney, Agent, or Firm* — C. A. Whealy

(57) ABSTRACT

A new and distinct cultivar of *Mandevilla* plant named 'MAN216901', characterized by its upright and vining plant habit; vigorous growth habit; freely branching habit; glossy green-colored leaves; early and freely flowering habit; and large bright white-colored flowers.

2 Drawing Sheets

Botanical designation: *Mandevilla sanderi.*
Cultivar denomination: 'MAN216901'.

BACKGROUND OF THE INVENTION

The present invention relates to a new and distinct cultivar of *Mandevilla* plant, botanically known as *Mandevilla sanderi* and hereinafter referred to by the name 'MAN216901'.

The new *Mandevilla* plant is a product of a planned breeding program conducted by the Inventor in De Kwakel, The Netherlands. The objective of the breeding program is to create new *Mandevilla* plants with large and attractive flowers.

The new *Mandevilla* plant originated from a cross-pollination conducted by the Inventor in De Kwakel, The Netherlands in August, 2011 of a proprietary selection of *Mandevilla sanderi* identified as code number 11-0006, not patented, as the female, or seed parent with a proprietary selection of *Mandevilla sanderi* identified as code number 11-0001, not patented, as the male, or pollen, parent. The new *Mandevilla* plant was discovered and selected by the Inventor as a single flowering plant from within the progeny of the stated cross-pollination in a controlled greenhouse environment in De Kwakel, The Netherlands in May, 2014.

Asexual reproduction of the new *Mandevilla* plant by cuttings in a controlled greenhouse environment in De Kwakel, The Netherlands, since August, 2014 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'MAN216901'. These characteristics in combination distinguish 'MAN216901' as a new and distinct *Mandevilla* plant:

1. Upright and vining plant habit.
2. Vigorous growth habit.
3. Freely branching habit.
4. Glossy green-colored leaves.
5. Early and freely flowering habit.
6. Large bright white-colored flowers.

Plants of the new *Mandevilla* can be compared to plants of the female parent selection. Plants of the new *Mandevilla* differ primarily from plants of the female parent selection in flower color as plants of the female parent selection have light pink-colored flowers.

Plants of the new *Mandevilla* can be compared to plants of the male parent selection. Plants of the new *Mandevilla* differ primarily from plants of the male parent selection in flower size as plants of the new *Mandevilla* have larger flowers than plants of the male parent selection.

Plants of the new *Mandevilla* can be compared to plants of *Mandevilla sanderi* 'Fisrix White', not patented. In side-by-side comparisons, plants of the new *Mandevilla* differ primarily from plants 'Fisrix White' in the following characteristics:

1. Plants of the new *Mandevilla* flower earlier than plants of 'Fisrix White'.
2. Plants of the new *Mandevilla* are more freely flowering than plants of 'Fisrix White'.
3. Plants of the new *Mandevilla* have larger flowers than plants of 'Fisrix White'.

4. Plants of the new *Mandevilla* and 'Fisrix White' differ in flower color as plants of 'Fisrix White' have light pink- colored flowers.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'MAN216901' grown in a container.

The photograph on the second sheet is a close-up view of a typical flowering plant of 'MAN216901'.

DETAILED BOTANICAL DESCRIPTION

The aforementioned photographs and following observations, measurements and values describe plants grown during the spring in 19-cm containers in a glass-covered greenhouse in De Kwakel, The Netherlands and under cultural practices typical of *Mandevilla* commercial production. During the production of the plants, day temperatures ranged from 20° C. to 22° C. and night temperatures averaged 18° C. Plants were pinched one time and were ten months old when the photographs and description were taken. In the following description, color references are made to The Royal Horticultural Society Colour Chart, 1995 Edition, except where general terms of ordinary dictionary significance are used.

Botanical classification: *Mandevilla sanderi* 'MAN216901'.

Parentage:

*Female, or seed, parent*.—Proprietary selection of *Mandevilla sanderi* identified as code number 11-0006, not patented.

*Male, or pollen, parent*.—Proprietary selection of *Mandevilla sanderi* identified as code number 11-0001, not patented.

Propagation:

*Type*.—By vegetative cuttings.

*Time to initiate roots, summer*.—About 21 days at temperatures about 22° C.

*Time to initiate roots, winter*.—About 27 days at temperatures about 22° C.

*Time to produce a rooted young plant, summer*.—About 40 days at temperatures about 22° C.

*Time to produce a rooted young plant, winter*.—About 50 days at temperatures about 22° C.

*Root description*.—Medium in thickness, fibrous to slightly fleshy; typically white in color, actual color of the roots is dependent on substrate composition, water quality, fertilizers, substrate temperature and physiological age of roots.

*Rooting habit*.—Freely branching; medium density.

Plant description:

*Plant and growth habit*.—Upright and vining plant habit; vigorous growth habit.

*Plant height, soil level to top of foliar plane*.—About 50 cm.

*Plant height, soil level to top of floral plane*.—About 60 cm.

*Plant diameter* (*spread*).—About 40 cm.

*Lateral branch description*.—Branching habit: Freely branching habit with about four primary each with about three to five secondary lateral branches developing per plant. Length: About 30 cm to 40 cm. Diameter: About 4 mm. Internode length: About 2 cm to 4 cm. Strength: Strong. Texture and luster: Smooth, glabrous; semi-glossy becoming woody and matte with development. Color, developing: Close to 143B. Color, developed: Close to 147C; when woody, close to 177D.

Leaf description:

*Arrangement*.—Opposite, simple.

*Length*.—About 6 cm to 7 cm.

*Width*.—About 4 cm.

*Shape*.—Ovate.

*Apex*.—Acuminate.

*Base*.—Obtuse.

*Margin*.—Entire.

*Texture and luster, upper and lower surfaces*.—Smooth, glabrous; leathery; glossy.

*Venation pattern*.—Pinnate.

*Color*.—Developing leaves, upper surface: Close to 144A. Developing leaves, lower surface: Close to 146C. Full expanded leaves, upper surface: Close to 139B; main vein, close to 143C and lateral venation, close to 139B. Fully expanded leaves, lower surface: Close to 146B; main vein, close to 143C and lateral venation, close to 146B.

*Petioles*.—Length: About 1 cm to 1.5 cm. Diameter: About 2 mm. Strength: Strong. Texture and luster, upper and lower surfaces: Smooth, glabrous; semi-glossy. Color, upper and lower surfaces: Close to 143C.

Flower description:

*Flower type and flowering habit*.—Single salverform flowers arranged in axillary cymes; flowers star-shaped and face upright to outwardly; freely flowering habit with about eight to nine flowers per inflorescence and about 180 flowers developing per plant during the flowering season.

*Natural flowering season*.—Plants flower continuously from late spring into late autumn in The Netherlands; plants begin flowering about seven months after planting.

*Flower longevity on the plant*.—About ten to twelve days; flowers not persistent.

*Fragrance*.—None detected.

*Inflorescence height*.—About 15 cm.

*Inflorescence diameter*.—About 15 cm.

*Flower buds*.—Length: About 7 cm. Diameter: About 1.2 cm. Shape: Elongated spindle-shaped. Texture and luster: Smooth, glabrous; semi-glossy. Color: Close to 145B; towards the base, close to 145D.

*Flowers*.—Appearance: Flared trumpet, corolla fused and five-parted. Diameter: About 8 cm to 9 cm. Depth (length): About 4 cm to 6 cm. Throat diameter: About 1.5 cm. Tube length: About 4 cm to 5 cm. Tube diameter, distally: About 4 mm.

*Corolla*.—Quantity and arrangement: Five petals arranged in a single whorl; proximal portion of the petals are fused into a tube; fee portions imbricate. Petal length: About 4 cm to 4.5 cm. Petal width: About 3 cm to 3.5 cm. Petal shape and appearance: Roughly spatulate. Petal apex: Acute. Petal margin: Entire; slightly undulate. Petal texture and luster, upper and lower surfaces: Smooth, glabrous; semi-glossy. Throat and tube texture: Smooth, glabrous. Color: Petal, when opening, upper surface: Initially, close to 145D becoming closer to 155C with development. Petal, when opening, lower surface: Close to 155C. Petal, fully opened, upper and lower surfaces: Close to 155C; venation, close to 155C; color does not change with development. Throat: Close to 2B; venation, close to 2B. Tube: Close to between 2D and 155C; venation, close to 155C.

*Calyx*.—Quantity and arrangement: Five sepals arranged in a single whorl; calyx, star-shaped. Length: About 5 mm to 8 mm. Diameter: About 6 mm. Sepal length: About 4 mm to 6 mm. Sepal width: About 2 mm. Sepal shape: Subulate. Sepal apex: Acute. Sepal margin: Entire. Sepal texture and luster, upper and lower surfaces: Smooth, glabrous; semi-glossy. Sepal color: When opening, upper and lower surfaces: Close to 145A. Fully opened, upper and lower surfaces: Close to 145A.

*Peduncles*.—Length: About 3 cm to 4 cm. Diameter: About 2 mm to 3 mm. Strength: Strong. Aspect: Mostly upright. Texture and luster: Smooth, glabrous; glossy. Color: Close to 144A.

*Pedicels*.—Length: About 2 cm. Diameter: About 2 mm. Strength: Strong. Aspect: About 30° from peduncle axis. Texture and luster: Smooth, glabrous; glossy. Color: Close to 144A.

*Reproductive organs*.—Stamens: Quantity and arrangement: Typically five; basifixed; anthers connivent. Filament color: Close to 12D. Anther length: About 6 mm to 8 mm. Anther shape: Narrowly oblong. Anther color: Close to 12D. Pollen amount: Moderate. Pollen color: Close to 12D. Pistils: Quantity: Typically one. Pistil length: About 1 cm to 1.5 cm. Style color: Close to 150B. Stigma shape: Club-shaped. Stigma color: Close to 150D. Ovary color: Close to 144A.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate temperatures ranging from 1° C. to 45° C.

It is claimed:

1. A new and distinct *Mandevilla* plant named 'MAN216901' as illustrated and described.

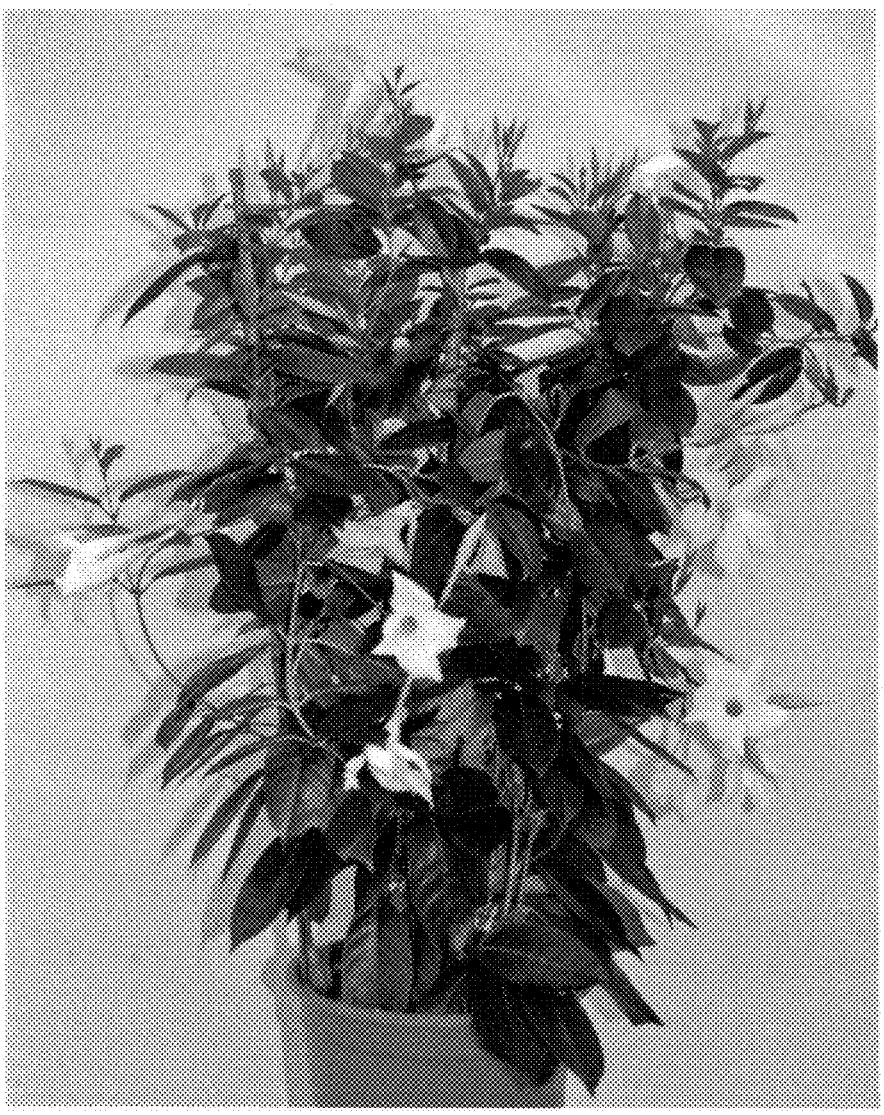

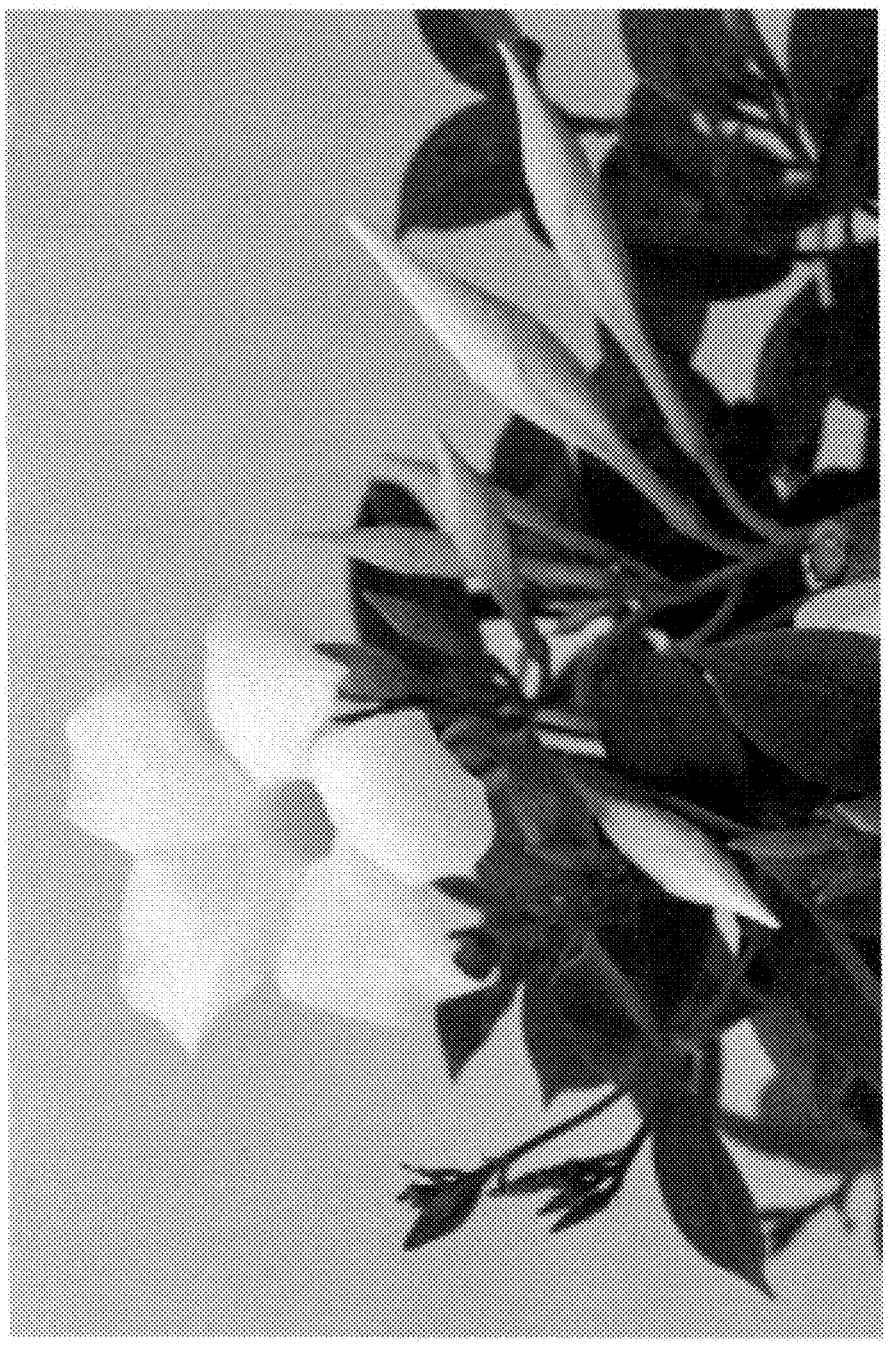

* * * * *